United States Patent [19]
Blom et al.

[11] Patent Number: 5,919,231
[45] Date of Patent: *Jul. 6, 1999

[54] DELIVERY SYSTEM FOR VOICE PROSTHESIS

[75] Inventors: Eric D. Blom; W. Gregory Chernoff; Daniel W. Karakla, all of Indianapolis, Ind.

[73] Assignee: Hansa Medical Products, Inc., Indianapolis, Ind.

[*] Notice: This patent is subject to a terminal disclaimer.

[21] Appl. No.: 08/408,225

[22] Filed: Mar. 22, 1995

Related U.S. Application Data

[60] Continuation-in-part of application No. 08/143,835, Oct. 27, 1993, abandoned, which is a division of application No. 07/818,853, Jan. 10, 1992, Pat. No. 5,300,119.

[51] Int. Cl.$^6$ ...................................................... A61F 2/20
[52] U.S. Cl. ................................. 623/9; 623/66; 604/14; 604/11
[58] Field of Search ................................. 604/11, 12, 13, 604/14, 15, 16, 17, 18; 623/9, 66

[56] References Cited

U.S. PATENT DOCUMENTS

| | | |
|---|---|---|
| 3,765,416 | 10/1973 | Werner et al. . |
| 4,246,897 | 1/1981 | Muto . |
| 4,291,690 | 9/1981 | Jessen . |
| 4,421,504 | 12/1983 | Kline . |
| 4,435,853 | 3/1984 | Blom et al. . |
| 4,596,579 | 6/1986 | Pruitt . |
| 4,610,659 | 9/1986 | Friese . |
| 4,614,516 | 9/1986 | Blom et al. . |
| 4,623,348 | 11/1986 | Feit . |
| 4,653,660 | 3/1987 | Shaw . |
| 4,676,773 | 6/1987 | Sheldon . |
| 4,690,671 | 9/1987 | Coleman et al. . |
| 4,695,275 | 9/1987 | Bruce et al. . |
| 4,900,303 | 2/1990 | Lemelson . |
| 4,911,687 | 3/1990 | Stewart et al. . |
| 4,911,716 | 3/1990 | Blom et al. . |
| 4,923,440 | 5/1990 | Genaro . |
| 4,964,850 | 10/1990 | Bouton et al. . |
| 5,041,080 | 8/1991 | Shimatani et al. . |
| 5,078,743 | 1/1992 | Mikalov et al. . |
| 5,090,420 | 2/1992 | Nielsen . |
| 5,108,421 | 4/1992 | Fowler . |
| 5,300,119 | 4/1994 | Blom . |

FOREIGN PATENT DOCUMENTS

| | | |
|---|---|---|
| 0 222 509 A2 | 5/1987 | European Pat. Off. . |
| 3121976 A1 | 3/1982 | Germany . |
| WO 88/02238 | 4/1988 | WIPO . |

*Primary Examiner*—Paul B. Prebilic
*Attorney, Agent, or Firm*—Barnes & Thornburg

[57] ABSTRACT

A device for insertion into a first opening in a body includes a device body having a longitudinal axis and a flexible first flange provided on an outside surface of the device body. The first flange has a deployed, use orientation in which it projects generally outwardly from the outside surface of the device body and an undeployed, insertion orientation in which it is resiliently deflected toward the device body. A retainer retains the flange in its insertion orientation. The retainer is constructed of a material soluble in a fluid.

7 Claims, 8 Drawing Sheets

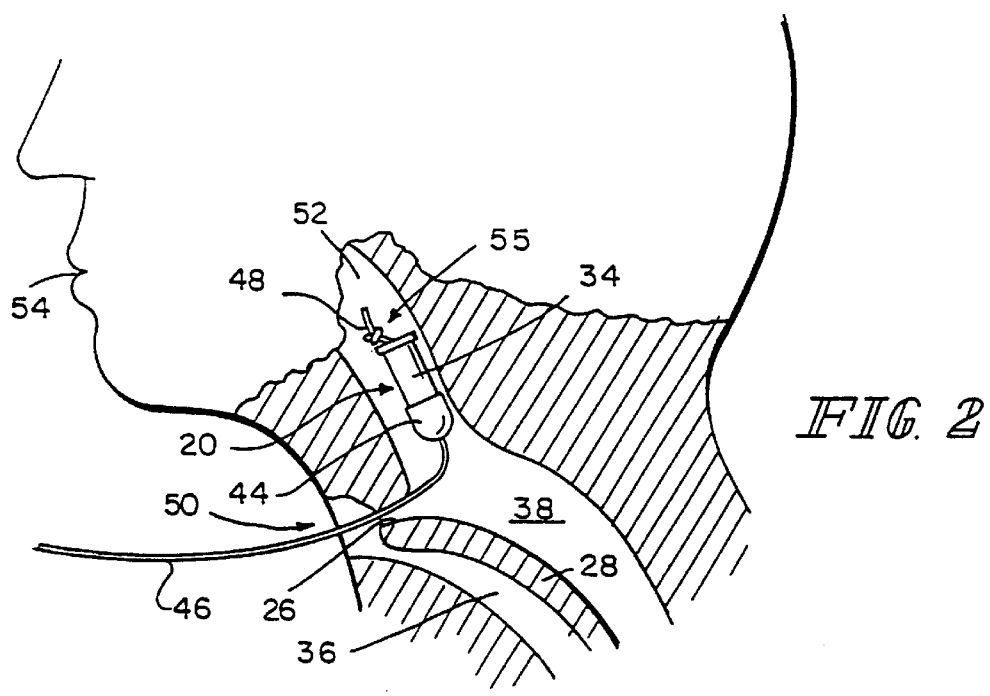
FIG. 2
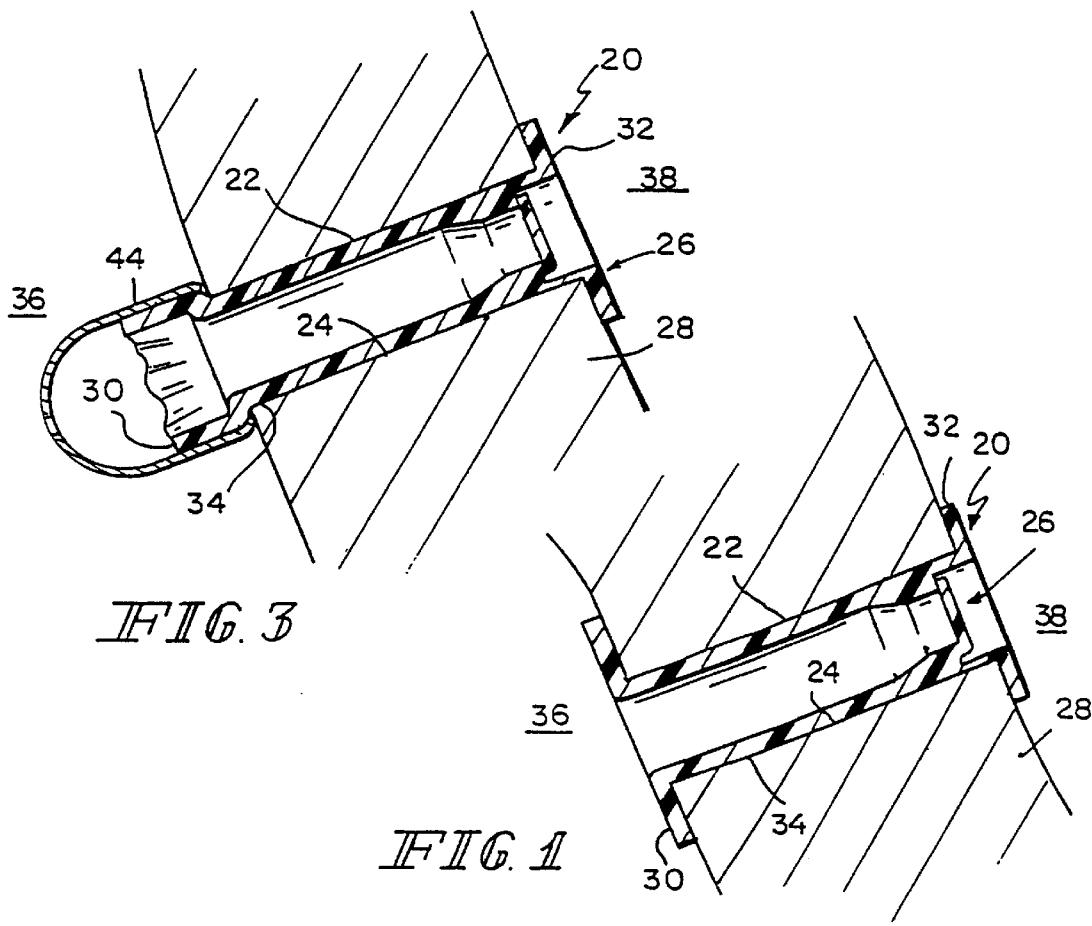
FIG. 3
FIG. 1

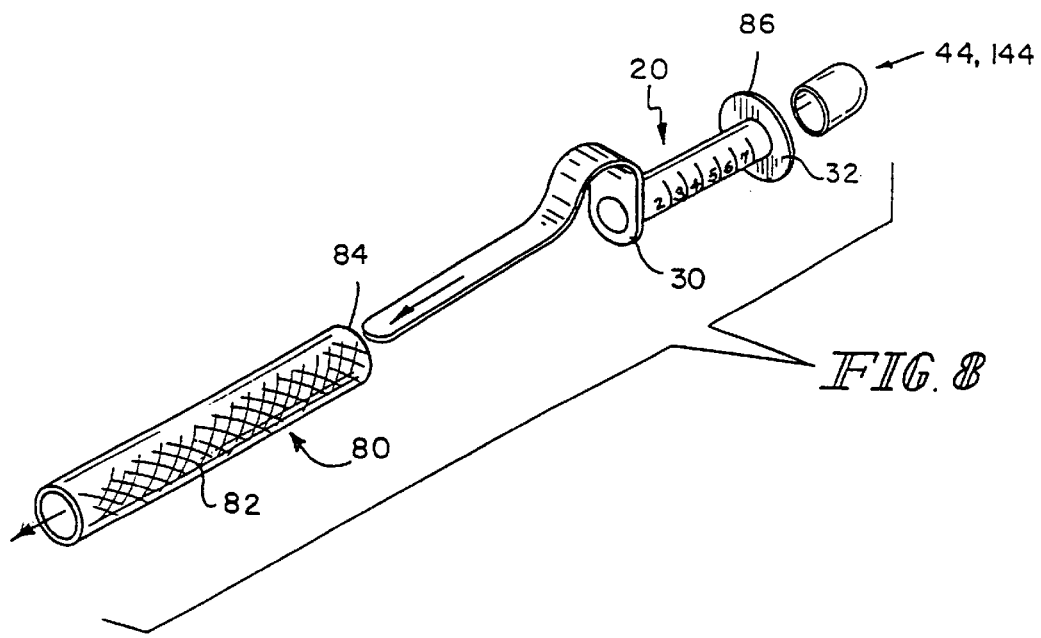
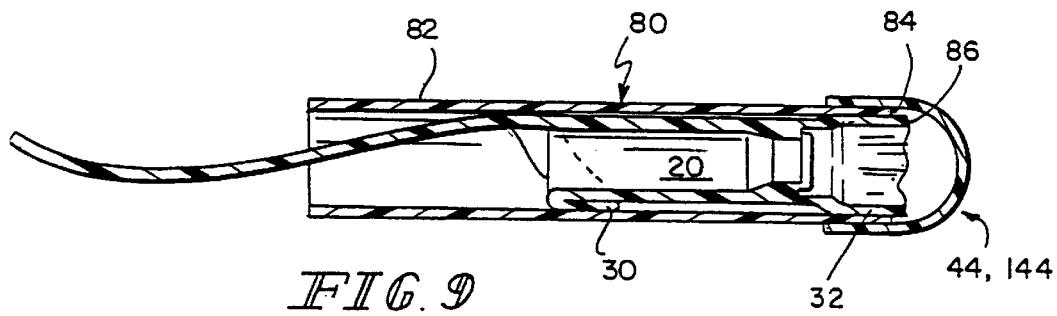
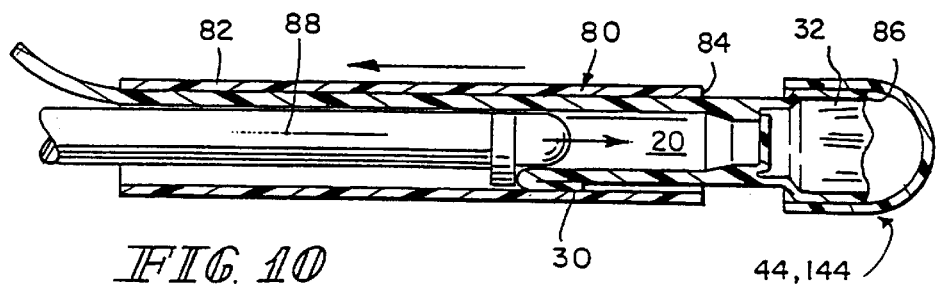

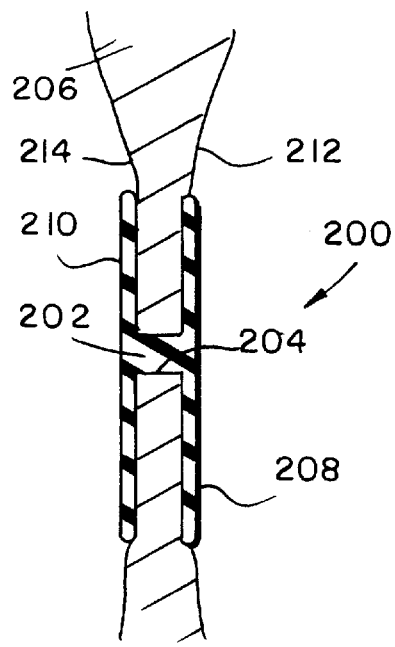
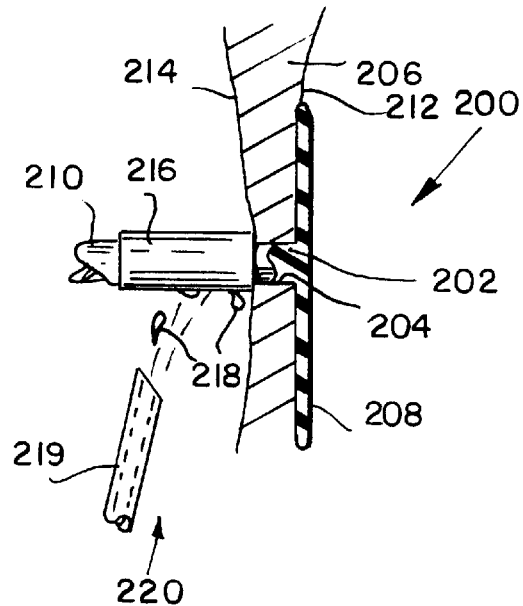
FIG. 14     FIG. 15
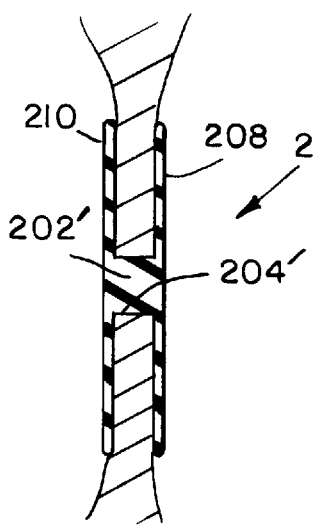
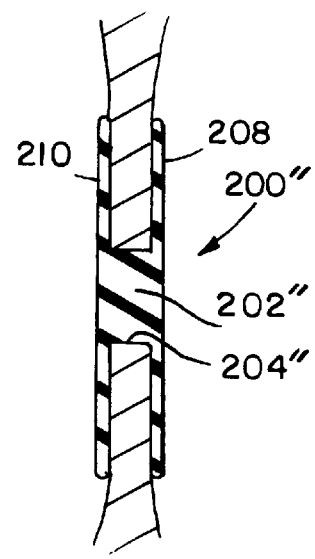
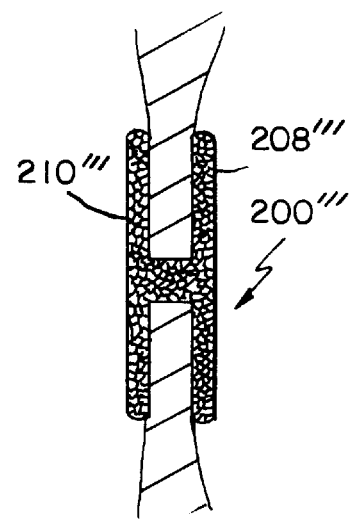
FIG. 14a     FIG. 14b     FIG. 16

DELIVERY SYSTEM FOR VOICE PROSTHESIS

This application is a continuation-in-part of U.S. Ser. No. 08/143,835 filed Oct. 27, 1993 (now abandoned) and assigned to the same assignee as this application. U.S. Ser. No. 08/143,835 is a division of U.S. Ser. No. 07/818,853 filed Jan. 10, 1992, now U.S. Pat. No. 5,300,119 dated Apr. 5, 1994.

This invention relates to a method and apparatus for the delivery, or placement, of, for example, a voice prosthesis device into a puncture provided in the tracheoesophageal wall of a speech restoration patient.

A speech restoration technique is known wherein air from the trachea is diverted from its normal flow path out through the tracheostoma to a flow path through a voice prosthesis providing a more or less permanent passageway to the esophagus. Esophageal speech results. See U.S. Pat. Nos. 4,435,853; 4,614,516; and 4,911,716. Voice prostheses currently in use for providing controlled air pathways through tracheoesophageal punctures incorporate flexible retention collars. The retention collar lies against the esophageal surface of the tracheoesophageal wall to reduce the likelihood of dislodgement of the prosthesis from the puncture. While this configuration substantially improves retention, the presence of the large retention collar makes insertion of a prosthesis more difficult and traumatic to the tissue surrounding the tracheoesophageal puncture. A possibility inherent in difficult or traumatic prosthesis insertion is incomplete insertion. Incomplete insertion may result in aspiration of the prosthesis into the airway. The prosthesis may be expelled by coughing, requiring endoscopic retrieval from the airway. Additionally, concern about prosthesis insertion difficulty may prevent some patients and physicians from employing this method of voice restoration.

According to an aspect of the invention, a device is provided for insertion into a first opening in a human body. The device includes a device body having a longitudinal axis and a flexible first flange provided on an outside surface of the device body. The first flange has a deployed, use orientation in which it projects generally outwardly from the outside surface of the device body and an undeployed, insertion orientation in which it is resiliently deflected toward the device body. A retainer retains the flange in its insertion orientation. The retainer is constructed of a material soluble in a fluid.

According to another aspect of the invention, a method is provided for inserting into a first opening in a human body a device including a device body having a longitudinal axis and a flexible first flange provided on an outside surface of the device body. The first flange has a deployed, use orientation in which it projects generally outwardly from the outside surface of the device body. The method comprises the steps of resiliently deflecting the flange toward the device body, placing over the resiliently deflected flange a retainer of a material soluble in a fluid, and inserting the device into the first opening.

Illustratively according to these aspects, the invention includes means for, or the step of, introducing the fluid into contact with the retainer.

Further illustratively according to these aspects, the first flange is positioned adjacent a first end of the device body which is inserted into the first opening.

Additionally, illustratively according to these aspects, a second flange is spaced along the device body from the first flange toward a second end of the device body.

Illustratively, the second flange is a flexible flange.

Further, illustratively according to these aspects, the invention includes an instrument for, or the step of, deflecting the flange to its insertion orientation to aid in placing the retainer around the deflected flange. The instrument has a second opening having a cross section slightly larger than a cross section of the device body transverse to its longitudinal axis.

Illustratively according to these aspects of the invention, the first opening is a first opening in a wall having a first side and a second side. The method further comprises the step of pushing the device body, resiliently deflected flange first, from the first side into the first opening so that the resiliently deflected flange lies on the second side of the wall.

Alternatively according to these aspects of the invention, the method comprises the step of pulling the device body, resiliently deflected flange first, from the second side into the first opening so that the resiliently deflected flange lies on the first side of the wall.

According to another aspect of the invention, a device for insertion into an opening in a human body includes a resiliently deflectable device body. The body has an insertion cross section transverse to its longitudinal extent which is insufficient to fill the opening and a larger use cross section transverse to its longitudinal extent. A retainer retains the device body in its insertion cross section. The retainer is removable to permit deployment of the device body to its use cross section.

According to yet another aspect of the invention, a method is provided for inserting into an opening in a human body a device. The device includes a resiliently deflectable device body having an insertion cross-section transverse to its longitudinal extent which is insufficient to fill the opening and a larger use cross section transverse to its longitudinal extent. The method comprises the steps of resiliently deflecting the device body, placing over the resiliently deflected device body a retainer for retaining the device body in its insertion cross section, inserting the device with the retainer in place into the opening, and removing the retainer to permit deployment of the device body to its use cross section.

Illustratively according to these latter aspects of the invention, the retainer is soluble in a fluid.

Additionally illustratively according to these aspects, the invention further comprises means for, or the step of, introducing the fluid into contact with the retainer.

The term "cylindrical body", as used herein, means a body including a surface generated by a straight line parallel to another straight line moving in a closed path.

BRIEF DESCRIPTION OF THE DRAWINGS

The invention may best be understood by referring to the following detailed description and accompanying drawings which illustrate the invention. In the drawings:

FIG. 1 illustrates a fragmentary sectional view through the tracheoesophageal wall of a wearer of a voice prosthesis device according to the present invention and longitudinally through-the voice prosthesis device itself;

FIG. 2 illustrates a step in a method of insertion of the voice prosthesis device of FIG. 1 according to the invention;

FIG. 3 illustrates a further step in the method, a step of which is illustrated in FIG. 2;

FIGS. 8–10 illustrate steps in a method of placement of a retainer onto a speech prosthesis according to the present invention;

FIG. 14 illustrates a fragmentary sectional view of the septum of a human nasal cavity, with the septum containing a septal button;

FIG. 14a illustrates a fragmentary sectional view of the septum of a human nasal cavity, with the septum containing a septal button;

FIG. 14b illustrates a fragmentary sectional view of the septum of a human nasal cavity, with the septum containing a septal button;

FIG. 15 illustrates a fragmentary sectional view of the septum of a human nasal cavity, with the septum containing a septal button;

FIG. 16 illustrates a fragmentary sectional view of the septum of a human nasal cavity, with the septum containing a septal button;

Figure 5:
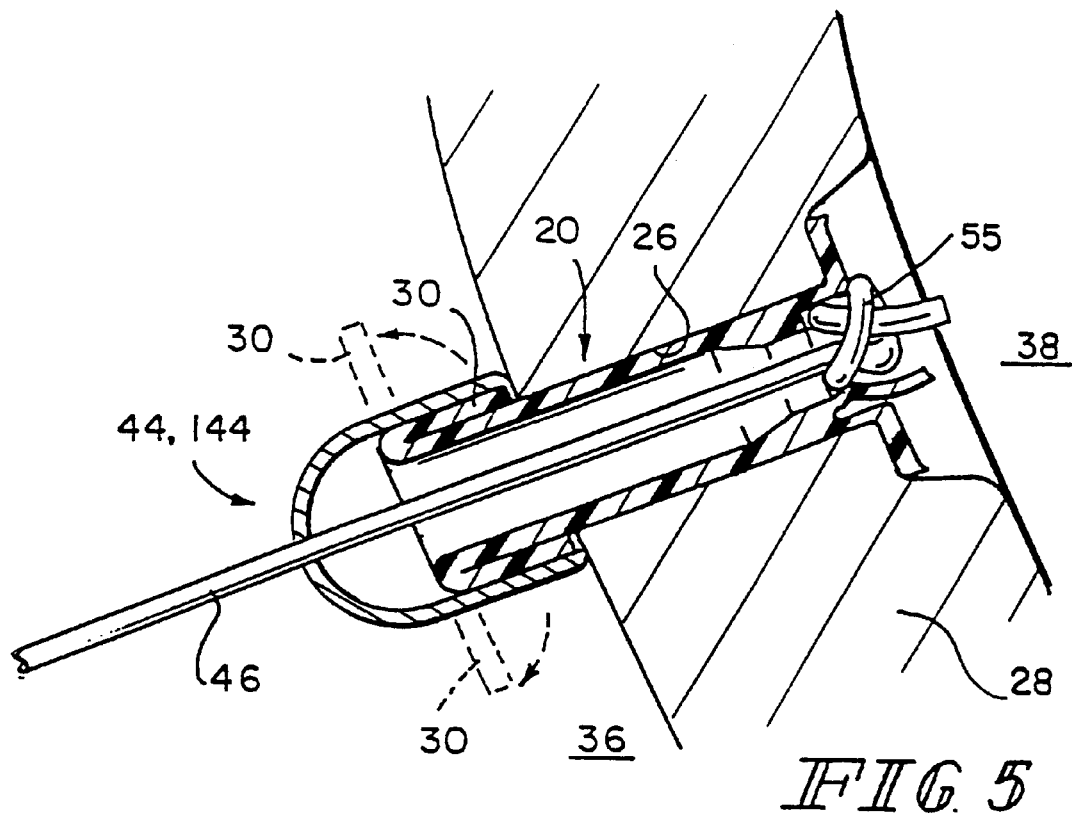
FIG. 5 illustrates a step in another method of insertion of the voice prosthesis device of FIG. 1 according to the invention.

Turning now to the drawings, a voice prosthesis device 20 includes a body 22 of a pliable silicone. The silicone must be rigid enough to withstand the forces placed upon it by the wall 24 of the puncture 26 through the tracheoesophageal wall 28 in which it resides. It must also be pliable enough to permit the folding of the retention flanges 30, 32 formed on its outside surface 34 adjacent its tracheal 36 and esophageal 38 ends, respectively. Flanges 30, 32 are responsible for positioning body 22 in the puncture 26 and reducing the likelihood of it being displaced in either the tracheal 36 or esophageal 38 direction.

Figure 6:
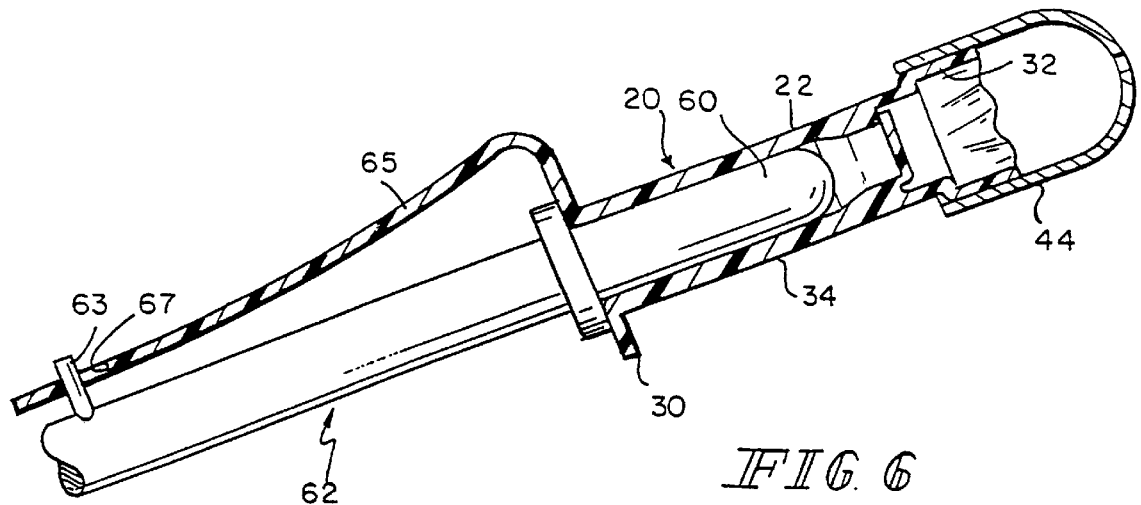
FIG. 6 illustrates a step in a method of insertion of the voice prosthesis device of FIG. 1 according to the invention.
Figure 7:
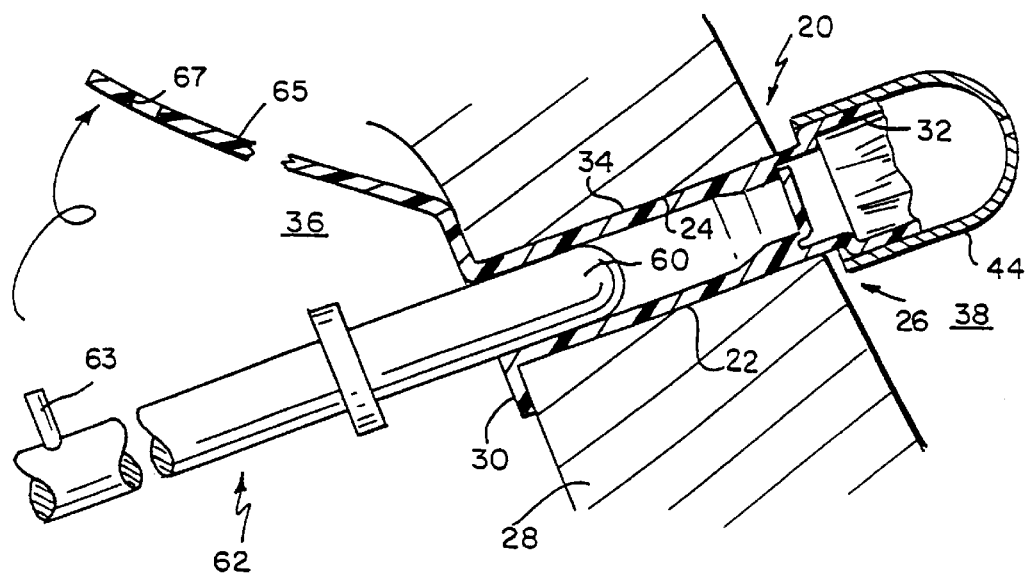
FIG. 7 illustrates a step in a method of insertion of the voice prosthesis device of FIG. 1 according to the invention.

Flanges 30, 32 are sufficiently flexible that they can be collapsed or folded into non-use, or insertion, orientations as illustrated by flange 30 in FIGS. 2–3 and flange 32 in FIGS. 6–7. Flanges 30, 32 are retained in these orientations by retainer 44 which illustratively may be cut-off portions of gelatin capsules. Once the voice prosthesis device 20 is inserted into the puncture 26, fluids such as saliva and the like, present in the tracheoesophageal wall 28 and the esophagus 38 dissolve the retainers 44 permitting the flanges 30, 32 to assume their use orientations illustrated in FIG. 1.

FIGS. 2 and 3 illustrate one method of delivery of a voice prosthesis 20 into a puncture 26. In this method, a pediatric catheter 46 (approximately French size 4), preferably, with a Cudé tip, is threaded through the tracheostoma 50, puncture 26 and upward through the pharynx 52 and out through the mouth 54 of a patient. The voice prosthesis 20 with flange 30 captured by a retainer 44 in folded, or insertion, orientation, is then threaded onto the tip 48 of the catheter 46. The retainer 44 is provided with a hole 53 in the tip thereof through which catheter 46 is threaded. A knot 55 is tied in the tip 48 of the catheter 46 to capture prosthesis 20 thereon, and the catheter 46 is pulled back downward through the pharynx 52 and puncture 26. This properly locates voice prosthesis 20 with flange 32 in its deployed, use, orientation and flange 30 still captured in its folded, non-use orientation. However, as retainer 44 is exposed to secretions and the like in the esophagus 38 and tracheoesophageal wall 28, retainer 44 dissolves and flange 30 deploys to its use orientation, positioning prosthesis 20 in puncture 26. Of course, catheter 46 may be removed at any time once voice prosthesis 20 is in place in the puncture, but the clinician may choose to wait to remove catheter 46 until flange 30 is deployed. The catheter 46 is removed by threading it back up through the pharynx 52, out through the mouth 54, untying the knot 55, and then pulling the catheter 46 out through the tracheostoma 50.

Figure 4:
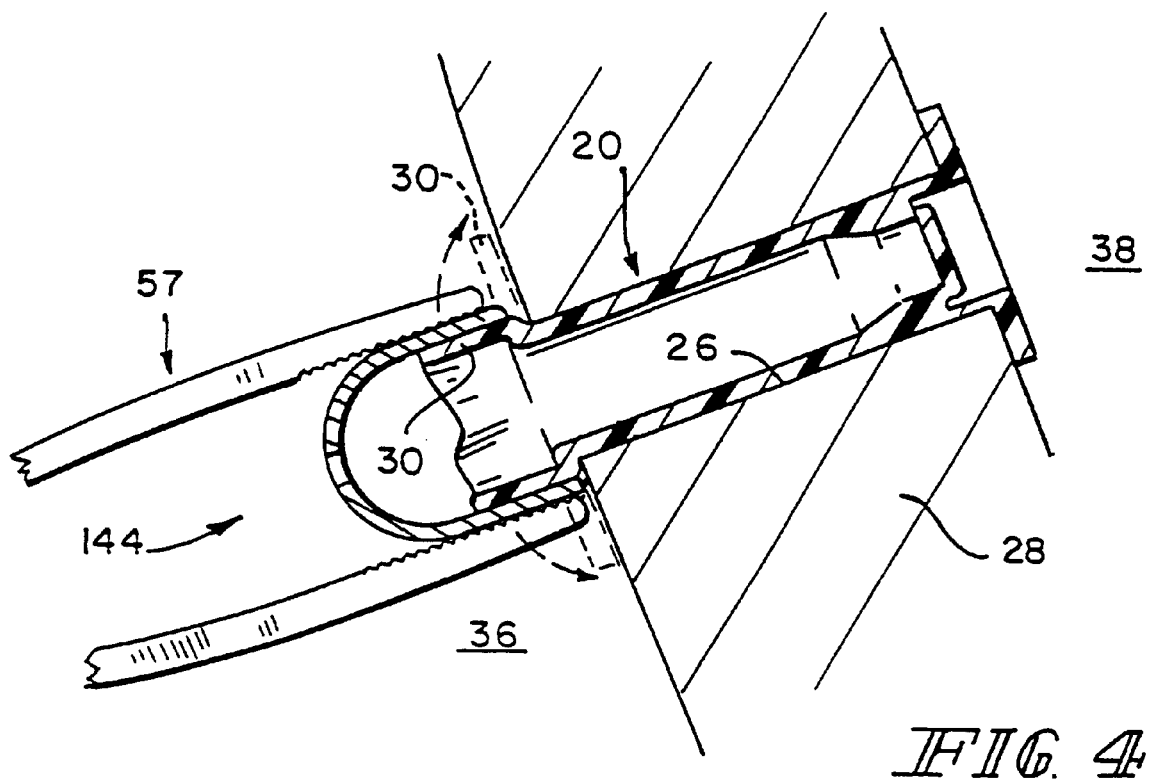
FIG. 4 illustrates a step in another method of insertion of the voice prosthesis device of FIG. 1 according to the invention.

Steps in two more insertion techniques are illustrated in FIGS. 4–5. In these techniques, a retainer 144 is employed which may or may not be soluble in fluids present in the tracheoesophageal wall and the esophagus. These methods work equally well in both cases. In these methods, the retainer 144 is placed over flange 30 to capture it in either forward folded (FIG. 4) or rearward folded (FIG. 5) orientation. The catheter 46 is located as in the embodiment of FIGS. 2–3 and the prosthesis 20 with retainer 144 thereon is threaded onto the catheter 46 and secured. The prosthesis is pulled downward through the pharynx 52 and located in the puncture 26. As illustrated in FIG. 4, the clinician then threads the catheter back up through the pharynx 52, unties the knot 55, and pulls the catheter 46 out. Finally, the clinician inserts a forceps, tweezers or the like 57 through the tracheostoma 50, removes the retainer 144 and pulls it out, deploying the flange 30 to its broken line position illustrated in FIG. 4.

A step in another technique for deploying flange 30 is illustrated in FIG. 5. In FIG. 5, flange 30 has been deflected rearwardly during the process of placing a retainer 44 or 144 on the leading end of prosthesis 20. As in the embodiment illustrated in FIG. 4, the catheter 46 is located as in the embodiment of FIGS. 2–3 and the prosthesis 20 with retainer 44 or 144 thereon is threaded onto the catheter 46 and secured. The prosthesis is then pulled downward through the pharynx 52 and into the puncture 26. However, instead of simply locating the prosthesis 20 correctly in the puncture 26, tension is maintained on catheter 46 sufficient to deflect the esophageal side 38 of the tracheoesophageal wall 28 toward the tracheal side 36 thereof. Then the retainer 44 is permitted to dissolve or the retainer 144 is removed as described in connection with FIG. 4, deploying flange 30 to its broken line orientation. Then the tension on catheter 46 is released, permitting prosthesis 20 to assume its proper orientation in puncture 26 and catheter 46 is removed, for example as described in connection with FIG. 4.

FIGS. 6 and 7 illustrate another method of delivery of a voice prosthesis 20 into a puncture 26. In this method, a retainer 44 is placed over flange 32, folding flange 32 into its non-use, or insertion, orientation. The voice prosthesis 20 is placed on the tip 60 of an insertion tool 62. Insertion tool 62 has a retainer peg 63. Voice prosthesis device 20 is provided with a strap 65 at its tracheal 36 end, illustratively formed on flange 30. Strap 65 is provided with an aperture 67 for accommodating peg 63 to retain prosthesis device 20 on tool 62 during insertion of device 20. Tool 62 is then manipulated through the tracheostoma (such as tracheostoma 50 in FIG. 2) of the wearer, and voice prosthesis 20 is inserted through the puncture 26. This properly locates voice prosthesis 20 with flange 30 in its deployed, or use, orientation and flange 32 still captured in its folded, non-use, orientation. However, as retainer 44 is exposed to saliva and the like on the esophageal 38 side of tracheoesophageal wall 28, retainer 44 dissolves and flange 32 deploys to its use orientation, positioning prosthesis 20 in puncture 26. Of course, tool 62 may be removed from prosthesis 20 at any time by removing strap 65 from peg 63, and then withdrawing tool 62. However, again, the clinician may choose to wait to remove tool 62 until flange 32 is deployed. Finally, since strap 65 is not needed once prosthesis 20 is inserted, strap 65 can be clipped from flange 30 and discarded.

FIGS. 8–10 illustrate steps in the loading of a flange, whether it be flange 30 or 32, into a retainer 44 or 144, to the orientation illustrated in FIGS. 2–4, 6 and 7. In the first step in the method, illustrated in FIG. 8, the prosthesis 20 is inserted into a thin-walled tube 80 to the orientation illustrated in FIG. 9. The outer sidewall 82 of tube 80 illustratively is knurled or otherwise textured to aid in gripping of the tube 80 during the process. Once the prosthesis has reached the orientation illustrated in FIG. 9, the retainer 44 or 144 is placed over the end 84 of the tube 80 from which the edge 86 of the folded flange 30 or 32 projects slightly. Then, referring to FIG. 10, a tool 88 of somewhat the same general configuration as tool 62 is pushed through the open end of the tube 80, engages the open end of prosthesis 20 and pushes prosthesis 20 out of tube 80 carrying the retainer 44 or 144 with it to retain flange 30 or 32 in its folded orientation illustrated in FIGS. 2–4, 6–7, 9 or 10. The prosthesis 20 is then ready for insertion using one of the methods described in connection with FIGS. 2–4 and 6–7. To load a flange 30 or 32 to the orientation illustrated in FIG. 5, the retainer 44 or 144 is simply pushed on an end of the prosthesis 20 deflecting the flange 30 or 32 along the length of prosthesis 20.

Figure 11:
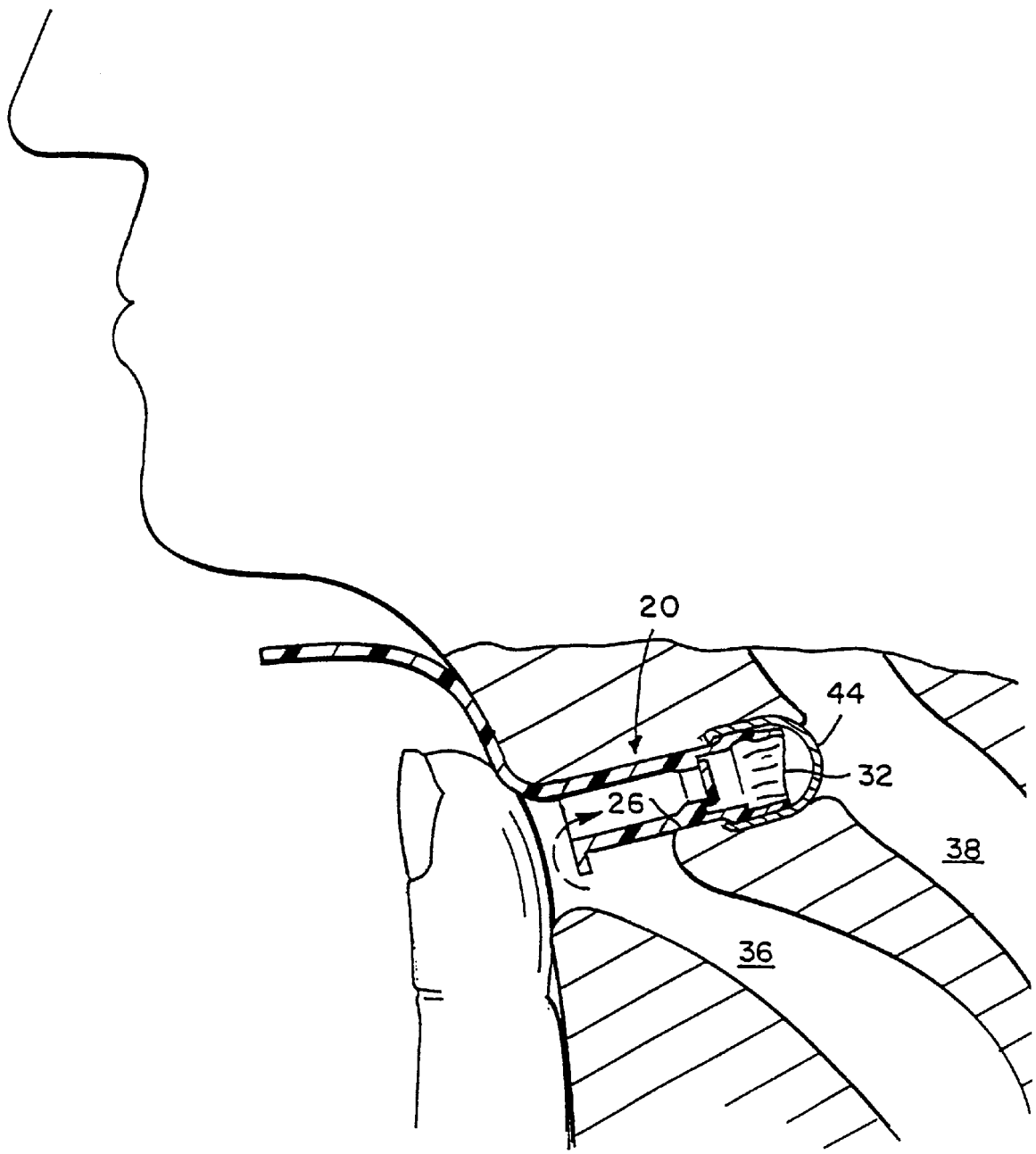
FIG. 11 illustrates a method for checking the placement of a speech prosthesis according to the present invention.

It is to be noted that if the insertion method, a step of which is described in connection with FIGS. 6–7, is employed, one test for proper deployment of the flange 32 is illustrated in FIG. 11. Namely, if the patient attempts to initiate esophageal speech through prosthesis 20 and too much force is required to get airflow through the prosthesis 20, that is an indication of incomplete deployment of the flange 32. This may mean that dissolution of the retainer 44 is incomplete and/or that the prosthesis 20 is too short to extend all the way through the puncture 26 from the tracheal end 36 to the esophageal end 38 thereof. This provides a convenient technique for use with the measuring probe which is used to measure the length of the puncture 26 between the trachea 36 and esophagus 38 to determine the correct length of prosthesis 20 for the patient.

Figure 12:
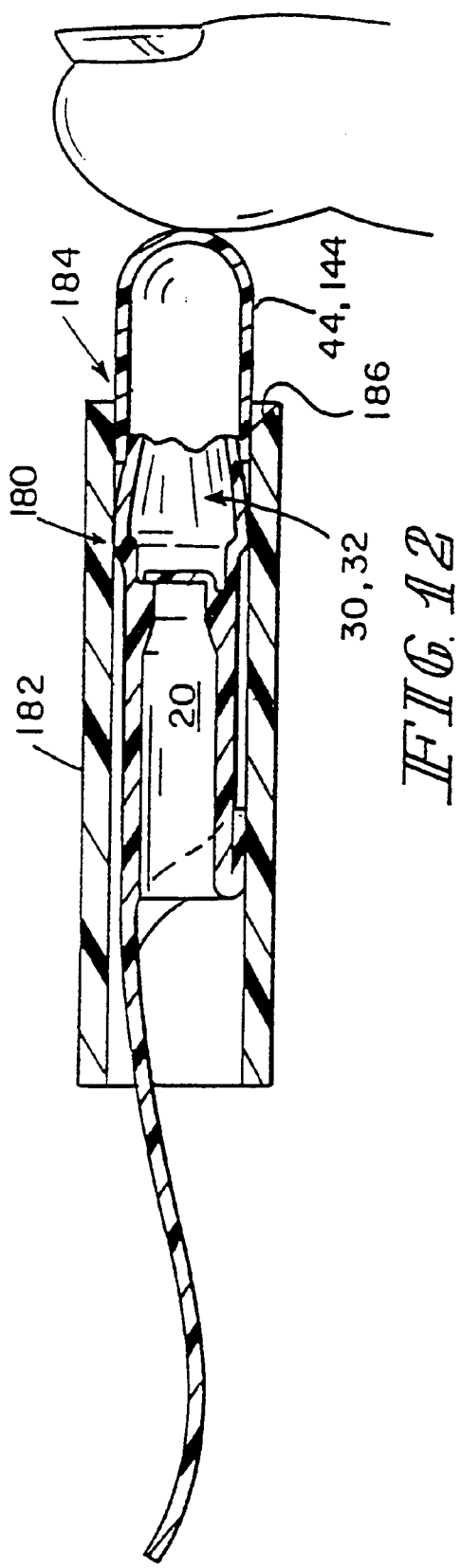
FIGS. 12–13 illustrate steps in a method of placement of a retainer onto a speech prosthesis according to the present invention.
Figure 13:
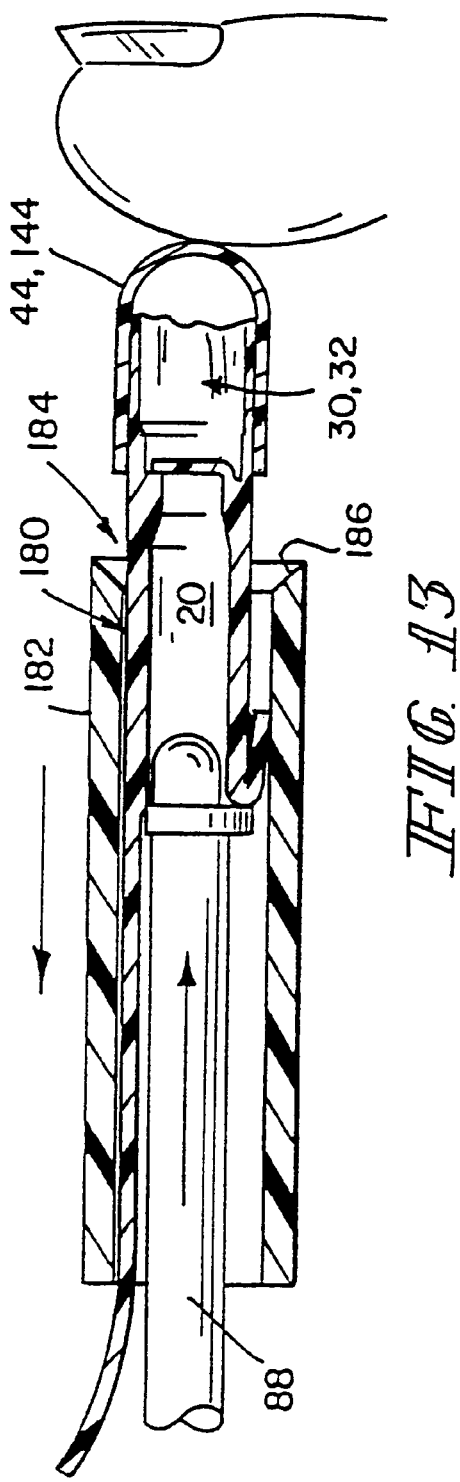

FIGS. 12–13 illustrate steps of an alternative method to that described in connection with FIGS. 8–10 for the loading of a flange 30 or 32 into a retainer 44 or 144, to the orientation illustrated in FIGS. 2–4, 6 and 7. In the first step in the method, illustrated in FIG. 12, the prosthesis 20 is inserted into a tube 180. The outer sidewall 182 of tube 180 again can be knurled or otherwise textured to aid in gripping of the tube 180 during the process. Once the prosthesis has reached the orientation illustrated in FIG. 12, the retainer 44 or 144 is placed inside the end 184 of the tube 180. The inside 186 of end 184 is bevelled slightly to help in folding the flange 30 or 32 and to guide retainer 44 or 144 into the end 184 of tube 180. The retainer 44 or 144 is held in the end 184 of tube 180 as prosthesis 20 is pushed out of tube 180 into retainer 44 or 144 by, for example, the clinician's forefinger while a tool 88 is pushed through the tube 180 (FIG. 13), engages the open end of prosthesis 20 and pushes prosthesis 20 out of tube 180, carrying the retainer 44 or 144 with it to retain flange 30 or 32 in its folded orientation illustrated in FIGS. 2–4, 6–7, 9 or 10. The prosthesis 20 is then ready for insertion using one of the methods described in connection with FIGS. 2–4 and 6–7.

In another embodiment constructed according to the invention, a septal button 200 has a central shaft 202 for plugging a perforation 204 in a nasal septum 206. Retaining flanges 208, 210 are provided at the ends of the shaft 202. Flanges 208, 210 are deployed to lie on opposite sides 212, 214, respectively, of the septum 206 when the septal button is in its use orientation, illustrated in FIG. 14. However, this deployed orientation of flanges 208, 210 makes it somewhat difficult to manipulate the septal button 200 into the perforation 204. To overcome this difficulty, a thin-walled, somewhat collar- or right circular cylindrically-shaped, soluble, gelatin retainer 216 is provided. One, 210, of flanges 208, 210 is collapsed into an insertion-aiding orientation, illustrated in FIG. 15, and retained in that orientation by slipping retainer 216 over it. Because there may not be sufficient moisture in the nasal mucosa to dissolve the retainer 216, resort may be had to different techniques to achieve timely deployment of flange 210 once the flange 210 in its insertion orientation has been manipulated through the perforation 204.

According to one technique, the retainer 216 is very slightly pre-wetted, that is, exposed to a solvent such as mild saline solution prior to insertion into the perforation 204. This results in a somewhat more timely dissolution of the retainer 216 and deployment of the flange 210. Pre-wetting makes the gelatin retainer 216 slightly slippery, which aids in insertion of the flange 210 through the perforation 204. Other solvents can be used to practice this technique. For example, a solvent can be employed that also functions as a lubricant for passage of the folded flange 210 and retainer 216. An example of such a solvent is glycerol. A solvent/lubricant aids in the passage of the folded flange 210 and retainer 216 through the perforation 204 and reduces trauma to the perforation 204 and surrounding septal tissue 206. This technique requires some experimentation to determine implantation and dissolution times so that the flange 210 does not deploy before it has passed through the perforation 204.

Another technique, illustrated in FIG. 15, that reduces the likelihood of premature deployment of the flange 210 is not to introduce the solvent 218 until after the folded flange 210 has been passed through the perforation 204. In this technique, the solvent 218, for example, mild saline solution, is introduced into contact with the retainer 216, for example, by injecting 219 the mild saline 218 up the affected nostril 220 after the septal button 200 is in place in the perforation 204.

As best illustrated in FIGS. 14a–b septal buttons 200', 200" having different sized shafts 202', 202", respectively, can be provided for different sized perforations 204', 204", respectively. A single, somewhat larger size flange 208, 210 can be used for all different sizes of shafts 202, 202', 202". Flanges 208, 210 can be cut to appropriate size prior to implantation.

Septal buttons 200, 200', 200" illustratively are constructed from resilient, medical grade silicones. However, FIG. 16 illustrates a non-permeable, non-absorbent, hypoallergenic closed cell foam septal button 200''' having flanges 208''', 210''' which can be folded and deployed in the same manner as described in connection with FIG. 15.

Figure 17:
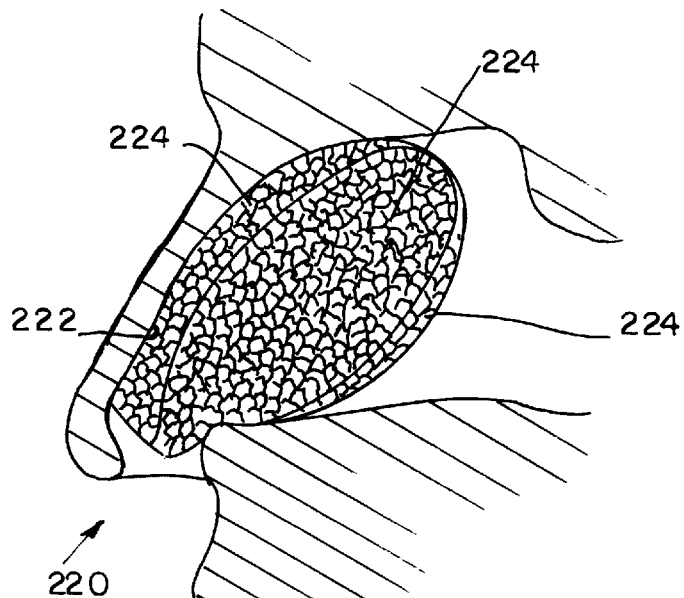
FIG. 17 illustrates a fragmentary sectional view of a human nasal cavity.

The present invention is also useful in inserting into passageways ducts, organs, and the like, devices which are not provided with locating or retaining flanges or the like. An example is illustrated in FIG. 17. Nasal packings and nasal packing insertion tools are known and are in common use. An example is the 4.5 cm nasal packing #400400 available from Merocel Corporation, Mystic, Conn. 06355, and its inserter. The packings are treated to render them rigid. This aids insertion. The inserter itself includes an elongate, syringe-like rigid plastic probe. The nasal tissues into which these are inserted typically have experienced recent trauma, and are tender and susceptible to further trauma. That is why the nasal packings are needed. Although the packings soften as they begin to absorb fluids from the traumatized tissue and nasal cavity, they are rigid when they are inserted, and they have a tendency to harden again a few hours after they have been put in place. Sometime later, they must, of course, be removed.

Figure 18:
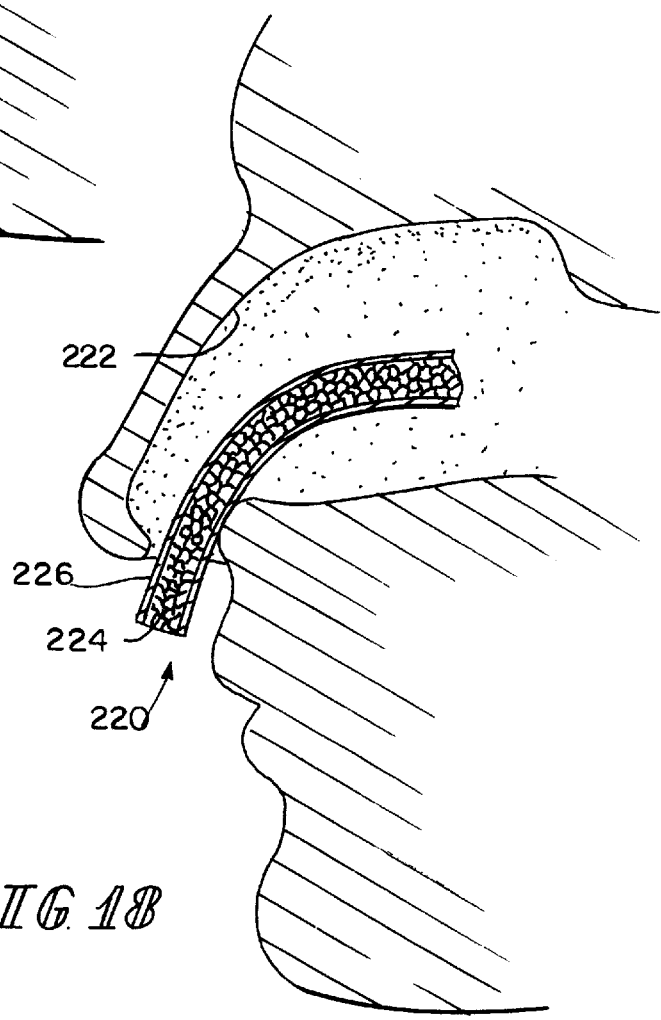
FIG. 18 illustrates a fragmentary sectional view of a human nasal cavity.

According to the invention, a soft, pliable, absorbent, open cell foam is fashioned into packings 224 having any appropriate cross-sectional configuration. The packings 224, when fully deployed (three are illustrated in FIG. 17), are too large for convenient or comfortable insertion through a nostril 220 into a nasal cavity 222, particularly one which has recently experienced trauma. To remedy this, the packings 224 are compressed and inserted into thin-walled, sleeve-like, flexible gelatin retainers 226, FIG. 18. The packing 224-retainer 226 combination is flexible and of small enough cross sectional area, for example, to be inserted easily through nostril 220 into nasal cavity 222 without causing significant trauma. The fluids which are the reason why the packings 224 are necessary dissolve the gelatin retainers 226 and aid the deployment of the packings 224.

What is claimed is:

1. In combination, a device for insertion into a first opening in a body, the device including a device body having a longitudinal axis and a flexible first flange provided on an outside surface of the device body, the first flange having a deployed, use orientation in which it projects generally outwardly from the outside surface of the device body and an undeployed, insertion orientation in which it is resiliently deflected toward the device body, and a retainer for retaining the flange in its insertion orientation, the retainer being constructed of a material soluble in a fluid.

2. The combination of claim 1 further including means for introducing the fluid into contact with the retainer.

3. The combination of claim 1 wherein the first flange is positioned adjacent a first end of the device body which is adapted to be inserted into the first opening.

4. The combination of claim 3 and further comprising a second flange spaced along the device body from the first flange toward a second end of the device body.

5. The combination of claim 4 wherein the second flange is a flexible flange.

6. The combination of claim 1 further comprising an instrument for deflecting the flange to its insertion orientation to aid in placing the retainer around the deflected flange, the instrument having a second opening having a cross section slightly larger than a cross section of the device body transverse to its longitudinal axis.

7. In combination, a device for insertion into an opening in a body, the device including a resiliently deflectable device body having an insertion cross section transverse to its longitudinal extent which is insufficient to fill the opening and a larger use cross section transverse to its longitudinal extent, and a retainer for retaining the device body in its insertion cross section, the retainer being removable to permit deployment of the device body to its use cross section, the retainer comprising a retainer soluble in a fluid, the combination further comprising means for introducing the fluid into contact with the retainer.

* * * * *